United States Patent [19]

Yao

[11] Patent Number: 5,285,672
[45] Date of Patent: Feb. 15, 1994

[54] MULTIPURPOSE DYNAMIC CONTROLLED ATMOSPHERE CHAMBER

[75] Inventor: Chaoliang Yao, Houston, Tex.

[73] Assignee: Shell Oil Company, Houston, Tex.

[21] Appl. No.: 806,176

[22] Filed: Dec. 13, 1991

[51] Int. Cl.$^5$ .............................................. G01D 18/00
[52] U.S. Cl. ....................................... 73/1 G; 73/865.6
[58] Field of Search ................. 73/1 G, 865.6, 23.41, 73/31.01, 31.02, 31.03

[56] References Cited

U.S. PATENT DOCUMENTS

| | | | |
|---|---|---|---|
| 3,290,920 | 12/1966 | Novak | 73/1 G |
| 3,664,188 | 5/1972 | Kockott | 73/150 R |
| 3,693,401 | 9/1972 | Purt et al. | 73/1 G |
| 3,832,882 | 9/1974 | Schoen, Jr. | 73/1 G |
| 3,983,742 | 10/1976 | Suga | 374/57 |
| 4,407,152 | 10/1983 | Guth | 73/1 G |
| 4,663,958 | 5/1987 | Matthiessen | 73/1 G |
| 5,050,663 | 9/1991 | Rhoads et al. | 160/231.2 |

FOREIGN PATENT DOCUMENTS

| | | | |
|---|---|---|---|
| 2247505 | 5/1973 | Fed. Rep. of Germany | 73/1 G |
| 270378 | 7/1989 | German Democratic Rep. | 73/865.6 |
| 192839 | 11/1982 | Japan | 73/1 G |
| 183222 | 6/1968 | U.S.S.R. | 73/865.6 |
| 534724 | 2/1977 | U.S.S.R. | 73/1 G |
| 928291 | 5/1982 | U.S.S.R. | 73/1 G |

OTHER PUBLICATIONS

Dixon, S. W.; Vasta, J. F.; Freeland, L. T.; Calvo, D. J.; and Hemingway, R. E.; "A Multiconcentration Controlled Test Atmosphere System for Calibration Studies" (Am. Ind. Hyg. J. 45(2), 99-104, Feb. 1984).
Irikura, A. K., "The Dynamic Generation and Collection of Test Atmospheres" (Technical Progress Report WRC 218-82, Shell Development Company, Houston, Tex.) Apr. 1, 1983 pp. 1-23.
Joki, H. M. "Passive Dosimeters. I. An Evaluation of the 3M Brand Organic Vapor Monitor for Benzene Exposures" (Technical Process Report WRC 113-80, Shell Development Company, Houston, Tex.) pp. 1-11 & 33-43 Aug. 1980.
Anderson, C. C., et al, "Generation of Test Atmospheres of Toxic Substances for Air Sampling Methods Evaluation" (175th ACS National Meeting, Mar. 15, 1978) pp. 1-21.
Freeland, L. T., "An Industrial Hygiene Calibration Manifold", Am. Ind. Hyg. Assoc. J. 38(12) 712-720, Dec. 1977.
Perkin-Elmer Model ATD 50 Thermal Desorption Application Note No. 14, "The Generation of Reference Atmospheres for the Calculation of Diffusive Uptake Rates" (TDA-14, Perkin Elmer) pub. by Dec. 1991 3 pages.

*Primary Examiner*—Tom Noland

[57] ABSTRACT

A stainless steel exposure chamber utilizes either a gas cylinder standard or a permeation tube standard to generate the required test atmosphere. The concentrations of the contaminants in the chamber can be varied from lower parts per billion (ppb) to high parts per million (ppm) levels. The system is capable of testing several types of industrial hygiene samplers at the same time, under the same chamber conditions and at different orientations of the samplers. The chamber is also useful for the development and verification of industrial hygiene air-monitoring methods.

12 Claims, 4 Drawing Sheets

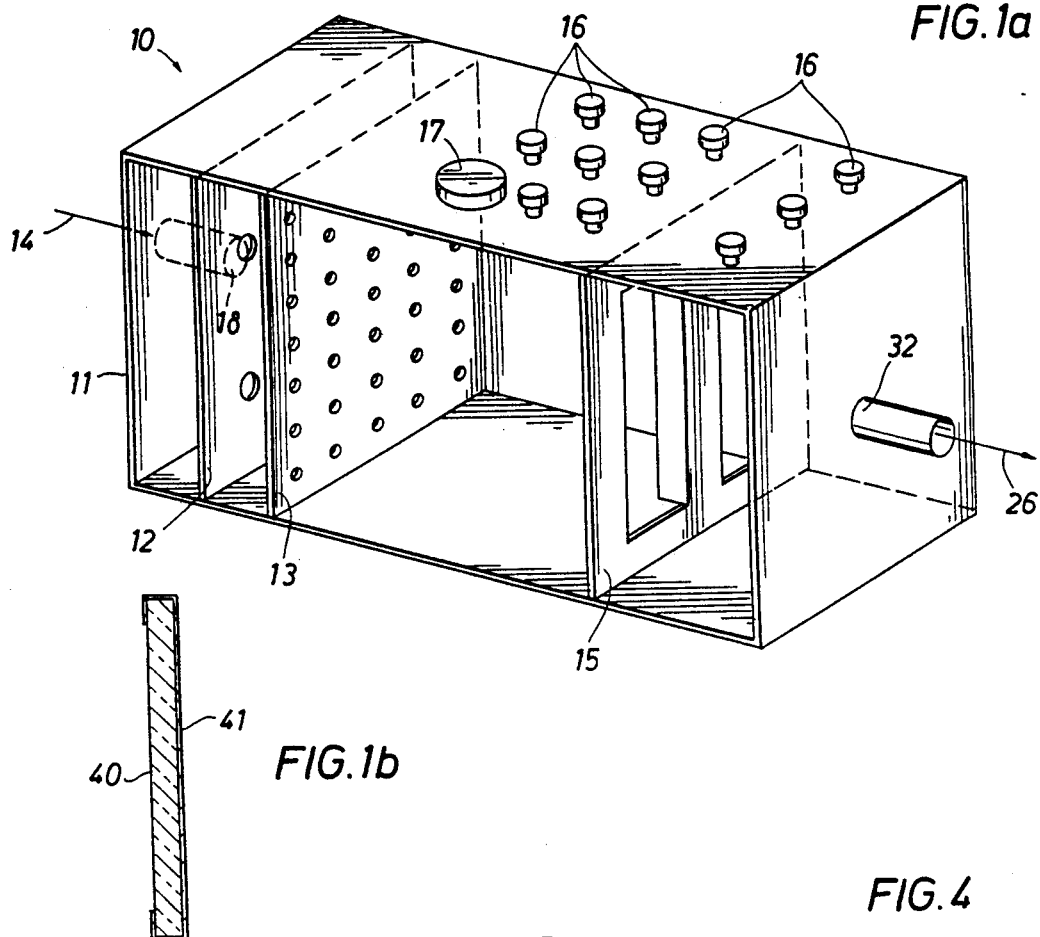
FIG.1a
FIG.1b
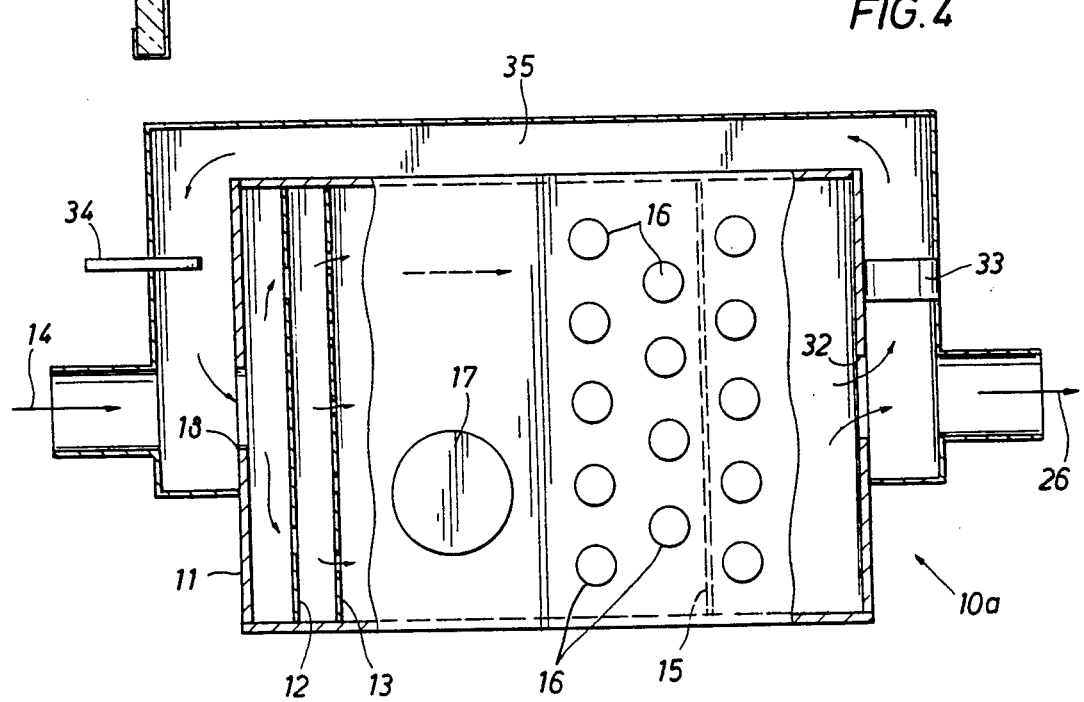
FIG.4

MULTIPURPOSE DYNAMIC CONTROLLED ATMOSPHERE CHAMBER

BACKGROUND OF THE INVENTION

1. Field of the Invention

The invention relates to dynamic, controlled atmosphere exposure testing chambers useful for the testing of industrial hygiene monitors and for the development and verification of industrial hygiene air monitoring methods.

2. Description of the Prior Art

Controlled atmosphere exposure chambers have been widely used for the development and validation of industrial hygiene laboratory air sampling methods. Since dynamic systems are usually employed in generating the desired atmosphere, a number of variables are involved in controlling the system performance. These variables include the concentration of the contaminants (analytes), humidity, temperature, linear velocity, and atmospheric matrices (such as benzene in the presence of various concentrations of gasoline vapor). Previously reported testing chambers were usually designed for one type of testing requirement with the article under test at a single orientation. As a result, different chamber designs are used for different testing devices. This made it difficult to perform a method comparison for different types of industrial hygiene monitors.

The article by Dixon, S. W.; Vasta, J. F.; Freeland, L. T.; Calvo, D. J.; and Hemingway, R. E., entitled "A Multiconcentration Controlled Test Atmosphere System for Calibration Studies" (Am. Ind. Hyg. J. 45(2), 99-104, 1984) reported a design of a controlled atmosphere test system. The design used a vacuum manifold with a Teflon tube chamber for testing active air monitors. It also used a separate, custom made linear exposure chamber constructed with Teflon-filled glass for testing passive dosimeters.

Irikura, A. K., in a report entitled "The Dynamic Generation and Collection of Test Atmospheres" (Technical Progress Report WRC 218-82, Shell Development Company, Houston, Tex.) reported a glass manifold test chamber with thirty pieces of ¼" o.d. Teflon tubing for testing the active charcoal monitors.

Joki, H. M., in a report entitled "Passive Dosimeters. I. An Evaluation of the 3M Brand Organic Vapor Monitor for Benzene Exposures" (Technical Progress Report WRC 113-80, Shell Development Company, Houston, Tex.) reported the use of a stainless steel manifold with six single dosimeter exposure chambers for testing passive dosimeters.

Anderson, C. C., et al, in an article entitled "Generation of Test Atmospheres of Toxic Substances for Air Sampling Methods Evaluation" (175th ACS National Meeting, Mar. 15, 1978) reported a cone-shaped exposure chamber with tube fittings for testing active sampling devices.

Freeland, L. T., in an article entitled "An Industrial Hygiene Calibration Manifold", Am. Ind. Hyg. Assoc. J. 38(12) 712-720, 1977 reported a jacketed glass sampling manifold for testing tube type industrial hygiene monitors.

Perkin-Elmer Model ATD 50 Thermal Desorption Application Note No. 14, entitled "The Generation of Reference Atmospheres for the Calculation of Diffusive Uptake Rates." (TDA-14, Perkin-Elmer) reported the design of an exposure chamber for testing tube-type diffusive passive dosimeters.

SUMMARY OF THE INVENTION

Applicant discloses the design and construction of a stainless steel exposure chamber which utilizes either a gas cylinder standard or a permeation tube standard to generate the required test atmosphere. In this chamber the concentrations of the contaminants can be varied from lower parts per billion (ppb) to high parts per million (ppm) levels. The system is easy to construct, simple to operate, and versatile enough to test several types of industrial hygiene samplers at the same time. While the invention is described in its preferred embodiment, stainless steel, other inert materials could be used, such as Teflon or PLEXIGLAS synthetic resin covered with a polyvinylfluoride fluoropolymer film sold under the trademark, TEDLAR.

In the industrial hygiene method validation and method development process, approval of any new type monitor, modified monitor, and/or modified sampling procedures requires the testing of the given monitor (either active or passive) in different contaminant concentrations and gas stream humidity inside a controlled atmosphere exposure chamber. Different linear face velocity tests are also required for validation of passive dosimeters and, if possible, the dosimeters should be tested with different face orientations with respect to the gas flow direction. The new and/or modified monitors or procedures should be compared with the existing ones under the identical test conditions. These tests require that the exposure chamber be able to accommodate various sampling devices at the pre-selected face velocity and face orientation, at the same time and under the same chamber conditions.

Several previously reported exposure chambers generally can only be used for testing the specific type of industrial hygiene monitors for which they are designed. Also, the existing linear exposure chambers for passive dosimeters only allow testing of the dosimeters while they are placed sequentially (i.e., serially) along the gas stream flow path. As a result, the concentration of the test contaminant in the gas stream is gradually decreased from the gas entrance side to the exit side due to the absorbance of the contaminant by the dosimeters. The dosimeters placed closest to the gas exit port tend to sample at a lower contaminant concentration, thus producing the so-called "starvation effect".

The new chamber described in this invention solves the problems encountered in previous designs by using multiple sampling ports on the chamber and by using different plug-in monitor holders inside the chamber. Those various plug-in sampler holders are designed for different test monitors having various face orientation and test gas flow rate requirements. They also allow placing of the passive dosimeters in parallel fashion inside the chamber equi-distant from the gas distribution baffles hence avoiding the problem caused by the depletion of test material concentrations along the gas stream flow path found in the linear exposure chamber.

The chamber possesses multiple functions for industrial hygiene air monitor testing and can be used to generate the dynamically controlled atmosphere for other testing requirements, such as controlled atmosphere corrosion tests and toxicity tests. It can also be used to generate a known concentration atmosphere as a calibration source for calibrating various gas detector sensors (for example, the sensors for $H_2S$, $SO_2$, etc.).

BRIEF DESCRIPTION OF THE DRAWINGS

FIG. 1a is an isometric drawing, partly in section of the controlled atmosphere exposure chamber of the present invention.

FIG. 1b is a sectional side view of the access door (front panel) of the exposure chamber of FIG. 1a.

FIG. 4 shows a modified exposure chamber with an air return duct.

DETAILED DESCRIPTION OF THE INVENTION

Figure 2:
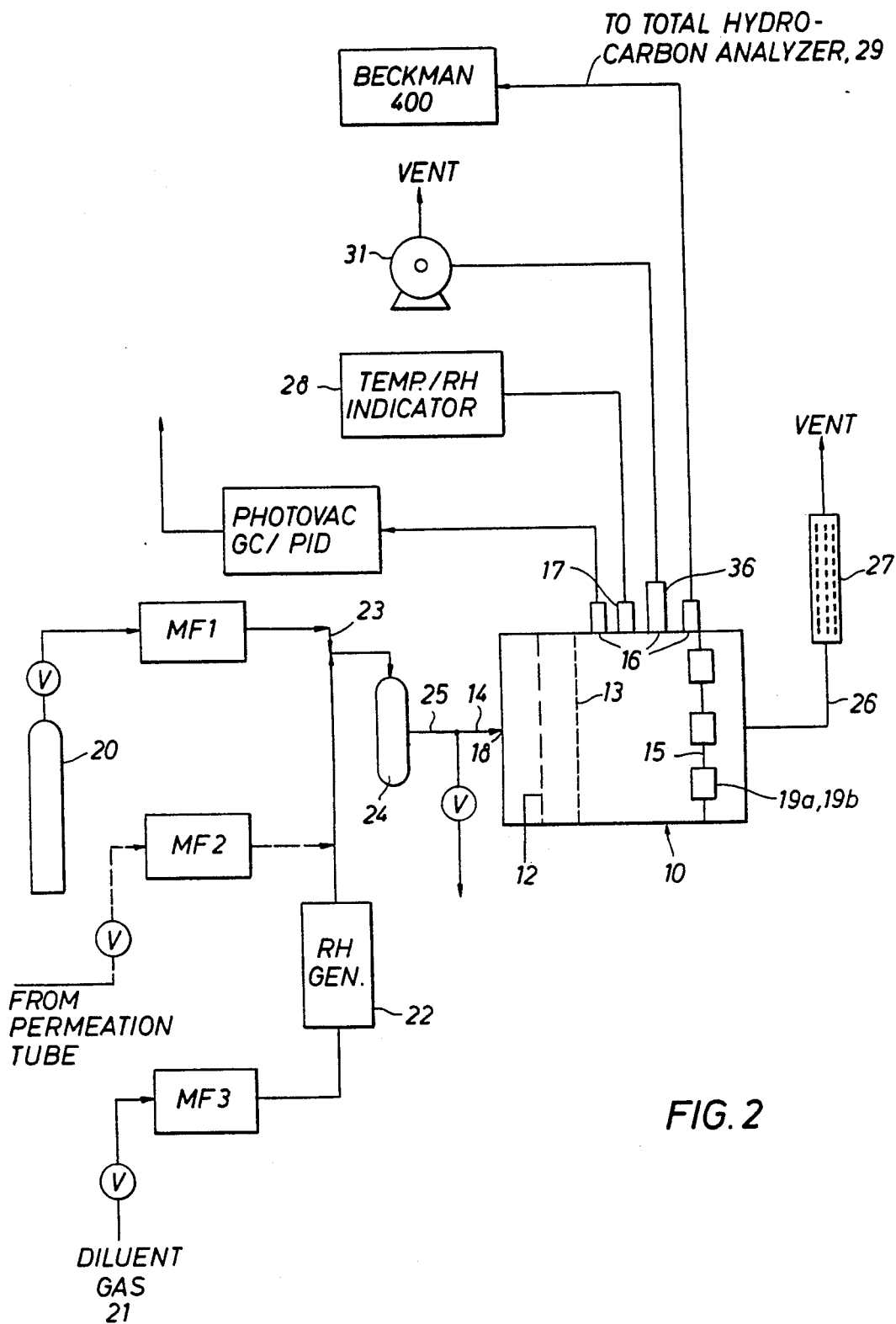
FIG. 2 is a schematic of the chamber of FIG. 1 as used in a testing environment.

The construction of the stainless steel exposure chamber 10 is illustrated in FIG. 1a. The access door 40, which comprises the entire front panel, has been removed for ease of illustration. The chamber walls 11 are preferably made from 16-gauge stainless steel. The front door or panel 40 (FIG. 1b) provides access to the chamber, forms one side of the enclosure and is preferably made of Plexiglas. To eliminate the problem caused from absorbing and desorbing the test contaminant by this material, the Plexiglas door 40 is preferably covered with a piece of film 41 cut from a large TEDLAR Film bag as shown in FIG. 1b. The TEDLAR Film bag is widely used for air sampling and is very inert towards most chemicals that would be used in the chamber. Test gas 14 is injected into chamber 10 through gas entrance port 18. There are two stainless steel baffle inserts 12, 13 to provide a uniform flow of the test gas stream 14 through the chamber 10. The third stainless steel insert 15 is used as a sampler hanger for either badge or tube-type passive samplers 19. A plurality of ¼" diameter Swagelok fittings are welded onto the top of the chamber 10. These fittings are used as sampling ports 16 for active sampling using industrial hygiene sampling pumps 31 and tube-type active industrial monitors 36 (such as charcoal collection tubes) and for associated test equipment 28, 29, 30 as shown in FIG. 2. A large access port 17 is used as a temperature/humidity indicator port.

The entire controlled atmosphere testing system flow diagram is illustrated in FIG. 2. The concentrated analytes are supplied either from the gas cylinder standard 20 obtained (for example) from Scott Specialty Gases Co. or from a Kin-Tek Model Span Lab 580-3C Precision Gas Standard Generator which uses a permeation standard tube. The diluent gas stream 21 is either laboratory house air or house nitrogen which is first humidified by passing it through a stainless steel humidity generator 22. It is then mixed with the analyte gas stream 23 in mixing chamber 24. The relative humidity is controlled by varying the ratio of the humidified gas and the dry gas stream. Both the gas mixing ratio and the total flow rate can be controlled with rotameters or digital mass flow controllers MF1, MF2, and MF3 such as Dyna-Blender Model No. 8280 manufactured by Matheson. The thorough mixing of analytes 23 with the diluent gas stream 21 is achieved in a glass mixing chamber 24 and a 5'×½" diameter length of Teflon tubing 25 before the gas 14 enters the exposure chamber 10. The exhaust gas 26 exits the chamber 10 through exhaust gas port 32 and is passed through a charcoal filter 27 to remove the contaminants before venting into a fume hood (not shown).

One of the Swagelok ports 16 on the chamber 10 is connected through a Teflon tubing to (e.g.) a Beckman Model 400 Hydrocarbon Analyzer 29. The concentration of a single component contaminant, or the total concentration of multiple component contaminant gas streams may be measured with this total hydrocarbon (THC) analyzer which is equipped with a flame ionization detector. A second port 16 is connected (e.g.) to a Photovac 10S70 gas chromatograph (GC) 30 equipped with a photoionization detector (PID). The concentrations of single or multiple contaminants can also be measured with this equipment at a 5-30 minute interval. The time weighted average (TWA) is calculated at the end of each exposure experiment. These instruments provide both continuous, real time THC and discrete GC analysis of the organic components in the chamber. The large port 17 on top of the chamber 10 is fitted with (e.g.) an Omega Model RH710 temperature and humidity probe which can output an analog signal for continuous recording of both the temperature and humidity on a chart recorder 28.

A large number of different designs of various industrial hygiene exposure monitors are used by the industry. They can be classified as a passive monitor 19 or an active monitor 36. The latter must be used with a personal sampling pump 31 to draw air through the monitor 36 during the exposure monitoring. Industrial hygiene exposure monitors may also be distinguished as tube or badge-shaped. While the Swagelok fittings 16 provide the access ports for the active monitors 36, the different types of sampler hangers 15 (shown in FIG. 3) used inside the chamber 10 are for the passive monitors 19a, 19b and allow the face of these samplers to be placed either parallel or perpendicular to the direction of the test gas stream 14 flow path according to the test requirements.

Figure 3A:
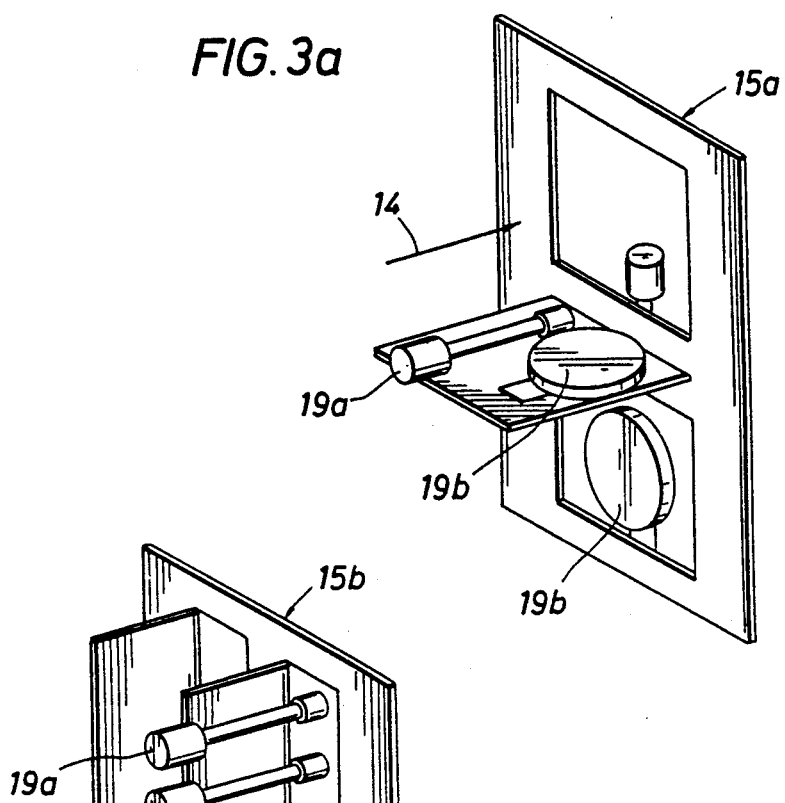
FIGS. 3a-3c, collectively referred to as FIG. 3, are illustrations of three different types of plug-in sampler hangers for passive dosimeters.
Figure 3B:
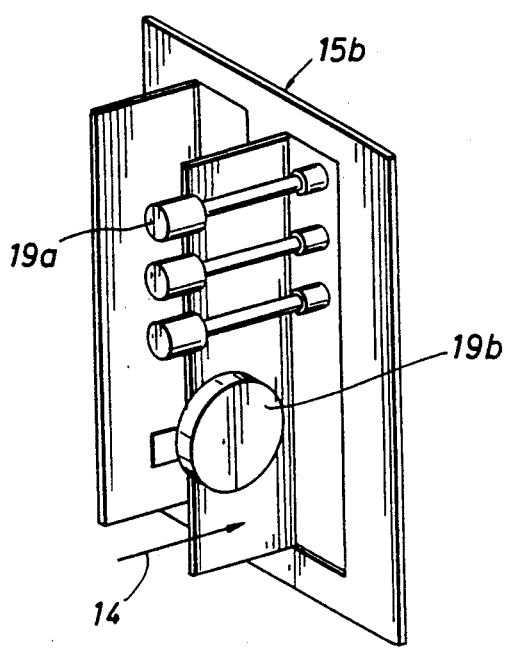
Figure 3C:
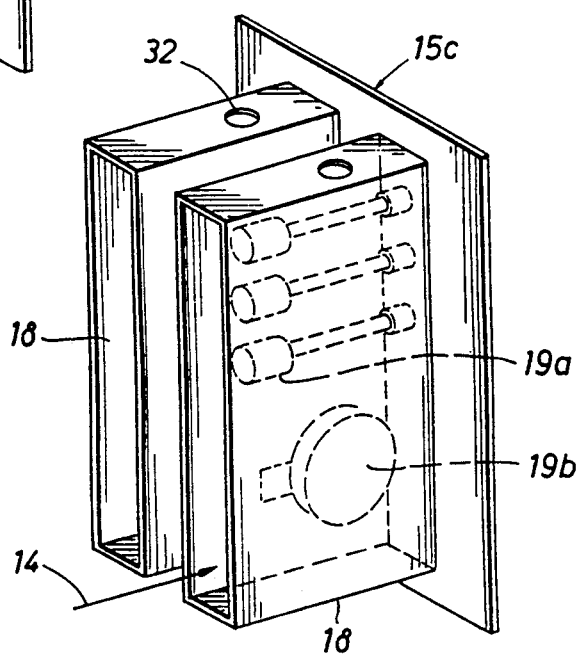

FIG. 3 shows three different sampler hangers 15a, 15b, 15c and possible placement of tube-type 19a or badge-type 19b passive dosimeters. The hanger 15a shown in FIG. 3a allows the face of the tube 19a and/or badge 19b passive monitors to be oriented parallel and/or perpendicular to the test air flow 14 direction. The hanger 15b shown in FIG. 3b allows the face of the tube monitor 19a to be oriented perpendicular to the air flow 14 while the face of the badge monitor 19b is oriented parallel to the air flow. The tunnel-shaped sampler hanger 15c shown in FIG. 3c is used for relatively high linear face velocity tests, where the gas stream 14 in the chamber 10 is forced through one or more "tunnels" 18 where dosimeters 19a, 19b are located. The "tunnels" 18 are box-like structures mounted on the hanger 15c having open, opposing sides for gas flow 14 therethrough toward the exhaust gas outlet port 32. The linear gas flow 14 velocity is measured with a wind velocity probe (not shown) inserted through one of the Swagelok fittings 16 and a hole 32 on the top of the tunnel 18.

The above mentioned exposure chamber 10 design allows studies requiring low to moderate linear face velocity (~50 ft/min) to be carried out on various types of passive dosimeters 19a, 19b. The higher linear velocity study used in some experimental designs, however, requires the modification of the exposure chamber 10 to avoid the consumption of too large an amount of the testing gas 14. Referring now to FIG. 4, an air return duct 35, which recycles part of the exiting exhaust air 26 back to the entrance port 18 of the chamber 10a, is added for this purpose. FIG. 4 shows the top view of chamber 10a after the addition of air duct 35. A variable speed fan 33 installed in the duct near exhaust gas outlet port 32 can deliver air at 0-9 ft$^3$/min. The dotted arrows indicate the air flow path with the air return duct 35 in use. Thus, the net air flow volume in the chamber 10a per unit of time is significantly increased even though the air stream input 14 to the entrance port 18 of the chamber 10a is unchanged. The exposure chamber air linear velocity can be further regulated with a damper 34 installed near the chamber gas entrance port 18. If a high linear velocity test is not required, the damper 34 can be closed to avoid leaking of the test gas 14 to the air duct 35. The maximum chamber linear velocity is about 200 ft/min with the modified exposure chamber 10a. Different linear velocities can be achieved with the use of different sampler hangers 15, fans 33, and/or chamber 10a cross sectional areas.

Figure 5A:
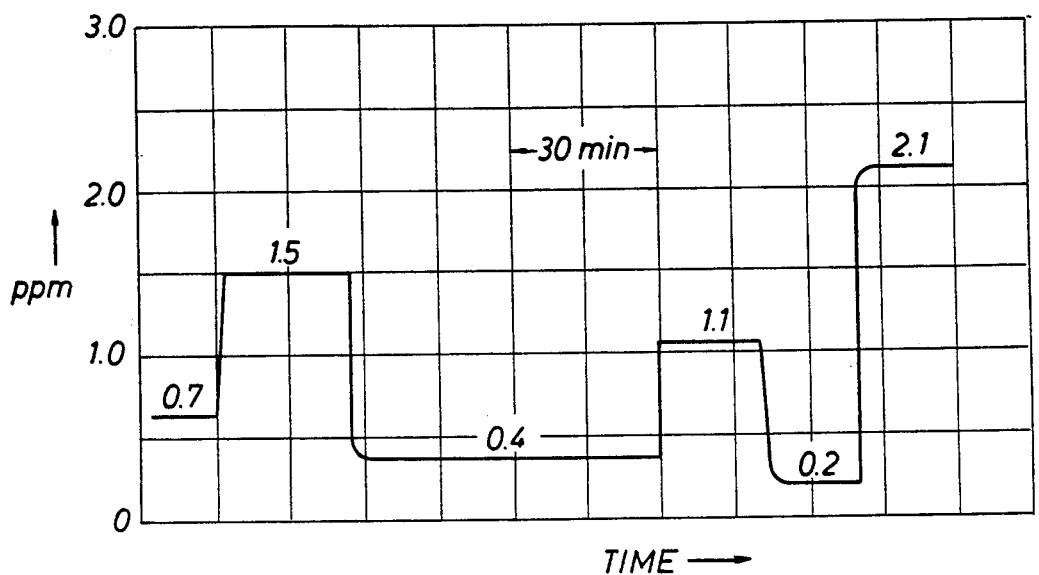
FIGS. 5a and 5b show plots of chamber concentration (ppm) vs. time for benzene and 1,3-butadiene in diluent gases.
Figure 5B:
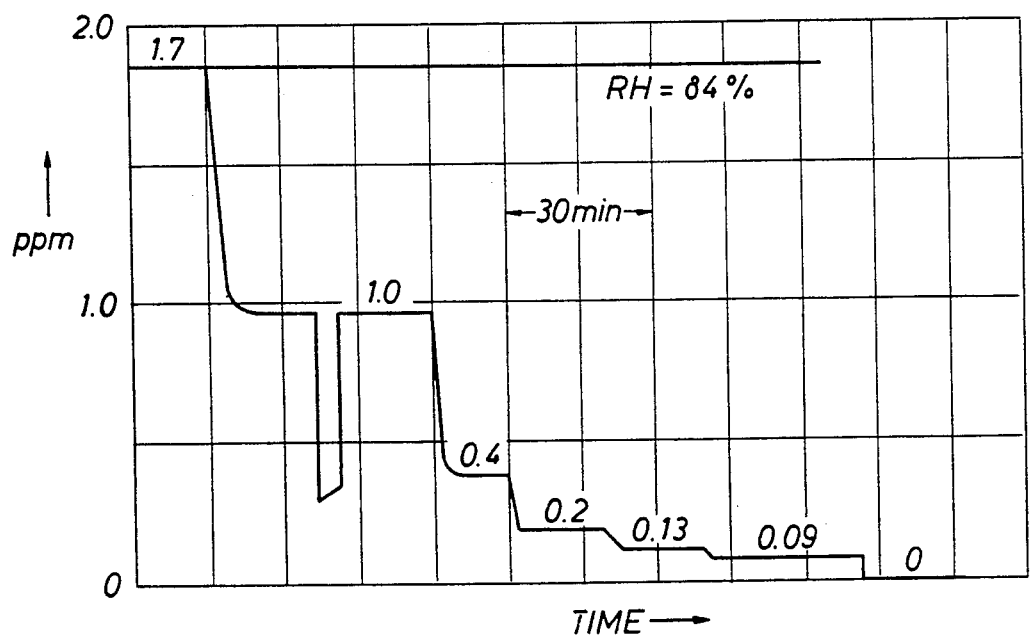

FIG. 5a illustrates the stepwise change of the gas concentration in the chamber 10 as the mixing ratio of benzene and diluent nitrogen is varied. The concentration of benzene in the chamber 10 is stepped from 0.7 ppm to 1.5, 0.4, 1.1, 0.2 and 2.1 ppm sequentially. FIG. 5b shows the stepwise change of the concentration of 1,3-butadiene (BD) in the chamber 10. The relative humidity (RH) is maintained at 84% and was stable during the entire experimental period.

If one assumes that there is ideally instantaneous mixing in the chamber 10, then the time constant for concentration changes in the chamber 10 can be calculated as:

$$tp/100 = -(V/F)\ln[(100-p)/100]$$

where t is the time in minutes, p is the percentage change in chamber concentration, V is the chamber volume in liters, F is the flow rate in L/min, and ln is the natural logarithm. Since the volume of the tested chamber is 4.7 L, the calculated $t_{0.5}$, $t_{0.95}$, and $t_{0.99}$ is then 0.5, 2.4, and 3.6 min, at a flow rate of 6 L/s, respectively. The obseved time it takes to reach 95% of the stepped concentration is on the order of 2-3 min (see FIG. 5), indicating that the chamber 10 has good mixing characteristics. Smaller time constants can be achieved with the use of higher gas flow rates.

APPLICATION EXAMPLES

The chamber 10 of FIG. 1 (without air duct 35) has been used experimentally in (1) developing the method to monitor personal exposure to 1,3-butadiene concentration in ambient air by passive sampling and thermal desorption; and (2) evaluating the limit of detection (LOD) and limit of quantitation (LOQ) of benzene in ambient air using 3M 3500 passive organic vapor monitors and SKC active charcoal monitors.

EXAMPLE 1

The exposure test BD with automatic thermal desorption (ATD) tubes were used to verify the performance of the exposure chamber 10. These tubes were packed with a 0.2 cm$^2$ wafer taken from the charcoal collection disk in a 3M 3500 organic vapor monitor and exposed on separate experiments in the exposure chamber 10 at various BD concentrations for 6 hours. The exposed tubes were then thermally desorbed into a GC for analysis. Several groups of SKC 226-37 charcoal tubes were also exposed with the ATD tube for comparison. The resulting data is listed in Table 1. Good agreement exists between results obtained from the concentration measured with the Photovac GC and from ATD tubes.

TABLE 1

| Analytical Data of BD Concentration in the Exposure Chamber | | | | | | | | |
|---|---|---|---|---|---|---|---|---|
| Photovac GC/PID | | | ATD Passive Dosimeters | | | SKC Charcoal Tubes | | |
| Mean (ppb) | N | CV (%) | Mean (ppb) | N | CV (%) | Mean (ppb) | N | CV (%) |
| 2150 | 16 | 1 | 2240 | 33 | 7 | | | |
| 1992 | 18 | 1 | 1996 | 12 | 8 | | | |
| 1963 | 19 | 3 | 1861 | 16 | 5 | 1940 | 5 | 3 |
| 1685 | 19 | 3 | 1757 | 7 | 4 | 1953 | 5 | 4 |
| 937 | 17 | 1 | 901 | 22 | 10 | | | |
| 642 | 16 | 1 | 699 | 17 | 12 | 708 | 5 | 5 |
| 426 | 9 | 7 | 473 | 11 | 16 | | | |
| 293 | 14 | 1 | 285 | 11 | 12 | 317 | 10 | 4 |
| 136 | 20 | 4 | 133 | 23 | 16 | 188 | 3 | 2 |
| 61 | 22 | 5 | 65 | 13 | 8 | | | |
| 25 | 22 | 5 | 27 | 34 | 17 | 25 | 6 | 6 |
| 20 | 20 | 3 | 24 | 11 | 8 | | | |
| 13 | 14 | 9 | 16 | 11 | 10 | | | |
| 8 | 16 | 6 | 10 | 11 | 12 | | | |

Linear regression equation:
Y = (−1.5) + 1.01X
Corr = 0.998
Y = 30.4 + 1.04X
Corr = 0.994

N is the number of data points (number of measurements for GC and number of ATD and SKC monitors used) in the experiments. CV is the coefficient of variation.

EXAMPLE 2

The current OSHA (Occupational Safety and Health Administration) Permissible Exposure Limit (PEL) for ambient air benzene concentration is 1 ppm on an 8-hour time-weighted average (TWA). However, the National Institute for Occupational Safety and Health (NIOSH) has recommended changing this occupational safety and health standard to 0.1 ppm. Similarly, the American Conference of Governmental Industrial Hygienists (ACGIH) also proposed the intended change to the benzene Threshold Limit Value (TLV) from the current 10 ppm to 0.1 ppm.

To accommodate the change in the reduced benzene exposure standard, Assignee's industrial hygiene laboratory has changed the benzene LOQ from 0.1 ppm to 0.01 ppm, based on liquid spiking experiments. The exposure tests for the purpose of testing the exposure chamber 10 performance and benzene LOD/LOQ were carried out on two types of industrial hygiene monitors (3M 3500 organic vapor monitor and SKC 226-01 charcoal tube) for benzene monitoring used by Assignee's manufacturing locations. The 3M monitor is a badge-type passive dosimeter and the SKC monitor is a tube-type active charcoal collection device. Seven SKC monitors were connected to the Swagelok fittings 16 and seven 3M monitors were placed on the sampler hanger 15 inside the testing chamber 10. The testing gas 14 was generated by blending a 100 ppm benzene standard gas with humidified air. Five sets of paired monitor groups were tested against testing chamber 10 concentration at 0.087, 0.036, 0.023, 0.012 and 0.006 ppm, respectively. The sample analysis of the monitors then follows NIOSH Method 1501 after the six hour exposure test. The analysis results showed that LOD and LOQ for 3M monitors were 0.002 and 0.006 ppm, while LOD and LOQ for SKC tubes were 0.003 and 0.009 ppm, respectively.

What is claimed is:

1. A dynamic, controlled atmosphere exposure testing chamber comprising:
   an enclosure having an air inlet port and an exhaust gas outlet port;
   means for introducing a pre-selected contaminant gas flow into said enclosure through said air inlet port;
   a gas diffusion baffle plate located inside said enclosure transversely of said enclosure and perpendicular to said gas flow direction;
   a hanger located inside said enclosure, essentially parallel to said baffle plate and downstream thereof with respect to said gas flow direction;
   a first industrial hygiene passive monitor mounted on said hanger;
   a plurality of sampling ports located in a wall of said enclosure downstream of said baffle plate;
   a first industrial hygiene active monitor connected to at least one of said sampling ports;
   a sampling pump connected to said active monitor;
   a gas chromatograph connected to one of said sampling ports;
   a total hydrocarbon analyzer connected to one of said sampling ports;
   an access port located in said enclosure wall;
   a temperature/relative humidity indicator connected to said access port; and
   means located external to said enclosure and connected to said outlet port for treating said contaminant gas before venting to the atmosphere.

2. The chamber of claim 1 wherein said enclosure is made of stainless steel.

3. The chamber of claim 1 wherein said chamber is equipped with a transparent door for access to the interior of said enclosure.

4. The chamber of claim 3 wherein the inside of said door is covered with an inert material.

5. The chamber of claim 4 wherein said material is a polyvinylfluoride fluoropolymer.

6. The chamber of claim 1 further including an air return duct, external of said chamber, said duct connecting said gas outlet port to said inlet port.

7. The chamber of claim 6 further including a fan located in said air return duct.

8. The chamber of claim 6 further including a damper located in said air return duct.

9. The chamber of claim 8 further including a fan located in said air return duct.

10. The chamber of claim 1 further including a second industrial hygiene passive monitor mounted on said hanger orthogonal to said first passive monitor.

11. The chamber of claim 1 wherein said hanger further includes a box-like structure mounted on said hanger, two opposing sides of said box-like structure being open, one of said open sides facing said air inlet.

12. The chamber of claim 11 further including at least one passive monitor mounted within said box-like structure.

* * * * *